US010435346B2

(12) United States Patent
Lord et al.

(10) Patent No.: US 10,435,346 B2
(45) Date of Patent: Oct. 8, 2019

(54) PROCESS FOR THE DISTILLATION OF AN ALDEHYDE MIXTURE (71) Applicant: JOHNSON MATTHEY DAVY TECHNOLOGIES LIMITED, London (GB)

(72) Inventors: Adrian Lord, London (GB); Martin Lucas Smidt, London (GB); Atul Manilal Shah, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 0 days.

(21) Appl. No.: 16/092,835

(22) PCT Filed: Apr. 13, 2017

(86) PCT No.: PCT/GB2017/051041
§ 371 (c)(1),
(2) Date: Oct. 11, 2018

(87) PCT Pub. No.: WO2017/182780
PCT Pub. Date: Oct. 26, 2017

(65) Prior Publication Data
US 2019/0119188 A1 Apr. 25, 2019

(30) Foreign Application Priority Data

Apr. 21, 2016 (GB) .................... 1606981.7

(51) Int. Cl.
*C07C 45/82* (2006.01)
*B01D 3/00* (2006.01)
*B01D 3/14* (2006.01)
*B01D 3/32* (2006.01)
*C07C 47/02* (2006.01)

(52) U.S. Cl.
CPC .............. *C07C 45/82* (2013.01); *B01D 3/148* (2013.01); *B01D 3/322* (2013.01); *B01D 3/324* (2013.01); *C07C 47/02* (2013.01); *B01D 2257/70* (2013.01)

(58) Field of Classification Search
CPC .......... C07C 45/82; B01D 3/148; B01D 3/324
See application file for complete search history.

(56) References Cited

U.S. PATENT DOCUMENTS

| 4,148,830 A | 4/1979 | Pruett |
| 4,247,486 A | 1/1981 | Brewster |
| 4,593,127 A | 6/1986 | Bunning et al. |
| 5,227,544 A | 7/1993 | Thurman et al. |
| 5,841,002 A | 11/1998 | Harrison et al. |
| 6,100,432 A | 8/2000 | Borgel et al. |
| 6,193,872 B1 | 2/2001 | Reason et al. |
| 6,511,583 B1 | 1/2003 | Muller et al. |

FOREIGN PATENT DOCUMENTS

| CN | 102580337 A | 7/2012 |
| DE | 3320648 A1 | 12/1984 |
| JP | BR PI0 718 007 A2 | 11/2013 |
| WO | WO 2008/056501 A1 | 5/2008 |

OTHER PUBLICATIONS

PCT/GB2017/051041, International Search Report dated Jul. 11, 2017.
PCT/GB2017/051041, Written Opinion dated Jul. 11, 2017.
GB1606981.7, Search Report under Section 17(5) dated Dec. 8, 2016.
GB1705980.9, Combined Search and Examination Report under Sections 17 and 18(3) dated Sep. 25, 2017.

*Primary Examiner* — Sikarl A Witherspoon
(74) *Attorney, Agent, or Firm* — BakerHostetler (57) ABSTRACT

A process for the distillation of an aldehyde mixture comprising a straight-chain aldehyde and a branched-chain aldehyde is described in which the process comprises: supplying a feed comprising the aldehyde mixture to a first separation vessel; operating said first separation vessel at a first temperature and a first pressure such that separation occurs; recovering a first stream comprising the straight-chain aldehyde from said first separation vessel and supplying said first stream to a second separation vessel; operating said second separation vessel at a second temperature and a second pressure such that separation occurs; recovering a product stream comprising the straight-chain aldehyde and a second stream comprising high-boiling components from said second separation vessel, and supplying said second stream to a third separation vessel; operating said third separation vessel at a third temperature and a third pressure such that separation occurs; and recovering a third stream comprising the aldehyde mixture from said third separation vessel and reintroducing said third stream to the first separation vessel.

17 Claims, 4 Drawing Sheets

PROCESS FOR THE DISTILLATION OF AN ALDEHYDE MIXTURE

CROSS-REFERENCE TO RELATED APPLICATIONS

This application is the National Stage of International Patent Application No. PCT/GB2017/051041, filed Apr. 13, 2017, which claims priority from Great Britain Patent Application No. 1606981.7, filed Apr. 21, 2016, the disclosures of each of which are incorporated herein by reference in their entireties for any and all purposes.

The present invention relates to a process for separating straight-chain and branched-chain aldehydes. The present invention particularly relates to a process for the separation of n-butyraldehyde and iso-butyraldehyde, which is also known as butanal. More particularly, the invention relates to an improved process for separating aldehydes, such as n-butyraldehyde and iso-butyraldehyde, at high yield and low cost. The process is particularly useful for the separation of straight-chain aldehydes from a mixture of straight-chain and branched-chain aldehydes and may allow the straight-chain aldehyde to be achieved at a purity of at least 95% and preferably at a purity of at least 98% and more preferably at a purity of at least 99% or at complete selectivity for the straight-chain aldehyde.

Mixtures of straight-chain and branched-chain aldehydes are typically formed as a result of hydroformylation processes. For example, butyraldehyde is produced almost exclusively by the hydroformylation of propylene. Traditionally, the hydroformylation of propylene was catalysed by cobalt carbonyl. More recently rhodium complexed with phosphine or phosphite ligands has been used as the catalyst. The hydroformylation reaction yields a mixture of n- and iso-butyraldehyde, which can be isolated in subsequent steps.

One of the uses of butyraldehyde is in the production of butanols. One use of n-butanol is in the production of butyl acrylate which is obtained by the esterification of n-butanol with acrylic acid. This is an important derivative as it is widely used as a solvent, flavour, fragrance and as a chemical intermediate or precursor for the production of other chemicals, such as emollients and plasticisers.

One of its most commercially significant uses of n-butanal is in the production of 2-ethylhexanol. In this reaction, pure n-butyraldehyde typically undergoes aldol condensation to form 2-ethylhexenal. The 2-ethylhexenal is then hydrogenated to form the intermediate 2-ethylhexanol. If iso-butyraldehyde is present during the aldol condensation reaction, then unfavourable reaction products are formed, such as ethylmethylpentanol. The presence of ethylmethylpentanol can be problematic. For example, its presence results in the formation of lower quality plasticisers. Accordingly, there is a need to produce substantially pure n-butyraldehyde by separating the n-butyraldehyde from a mixture of the n-butyraldehyde and the iso-butyraldehyde.

Similar issues are encountered with the separation of other straight-chain and branched-chain aldehydes that may be obtained from hydroformylation reactions, such as the production of $C_5$ aldehydes following the hydroformylation of butenes. For example, the linear $C_5$ aldehyde, which is known as 1-pentanal or n-valeraldehyde, is used in the production of 2-propylheptanol, which in turn is used to make plasticisers and which suffers from similar drawbacks to those discussed in connection with n-butyraldehyde. These drawbacks result from the presence of isomers of the 2-propylheptanol in the product such as 2-propyl,4-methylhexanol and 2-propyl,5-methylhexanol.

Whilst it is possible to alter the selectivity of the hydroformylation reaction to achieve a higher concentration of the desired normal isomer product by altering process variables, such as temperature, pressure and catalyst. However, it has not yet been possible to achieve the desired level of selectivity and desirably complete selectivity for the normal aldehyde isomer, and thus the products obtained from the hydroformylation process will be mixtures of both straight-chain and branched-chain aldehydes. In addition to the mixture of aldehydes, the product from the hydroformylation reaction will also comprise high-boiling components, which are known as heavies. These high-boiling components are formed by reactions between the components and may include dimers, trimers and tetramers. The formation of some of the high-boiling components is thought to occur by condensation reactions, such as aldol condensation reactions, Tischenko-type reactions or Cannizaro-type reactions. Discussions of these reactions and details of their mechanisms can be found in, for example, U.S. Pat. Nos. 5,841,002 and 6,193,872.

The product stream may also contain low-boiling components, which are known as lights. Lights which may be present may include one or more of unreacted alkenes, alkanes, and dissolved gases. Dissolved gases may include one or more of carbon monoxide, hydrogen, carbon dioxide, methane, nitrogen, argon and water. The produce stream may also include the corresponding alcohols that are formed by reduction of the aldehydes to alcohols during the hydroformylation process, water and alkanes.

As aliphatic aldehydes are readily condensed or polymerised by the action of heat and impurities, it was historically necessary to repeatedly fractionally distil the crude aldehydes obtained from the hydroformylation process in order to obtain products of sufficient purity.

In industrial processes, the separation of straight-chain and branched-chain aldehydes, such as the separation of n- and iso-butyraldehyde, may be achieved in two-step distillation processes that use two separate distillation columns. Taking the separation of n- and iso-butyraldehyde as an example, one such process is described in U.S. Pat. No. 5,102,505 column. The distillation conditions are selected such that the branched-chain aldehydes are taken off in liquid form in the upper region of the distillation column and the straight-chain aldehyde is separated into two distinct product streams. The first product stream of straight-chain aldehyde consists of essentially pure straight-chain aldehyde, which is taken off in vapour from the lower region of the distillation column. The second product stream of straight-chain aldehyde contains a major part of the high-boiling components, which is taken off at the bottom of the distillation column as the bottom product. It was, however, only possible to achieve at most 70% by weight of the straight-chain aldehyde present in the crude product.

An alternative arrangement is discussed in U.S. Pat. No. 6,511,583, where a first distillation column separates a stream of butyraldehyde from the high-boiling components. A stream comprising n-butyraldehyde is taken as a side draw from the first distillation column and a stream containing both n-butyraldehyde and high-boiling components is also taken from the bottom of the first distillation column. The stream taken from the bottom of the first distillation column is separated in a second distillation column to a more concentrated stream comprising high-boiling components and a stream comprising mainly n-butyraldehyde, which is fed back into the first distillation column.

Whilst the two-step process does allow some separation, various disadvantages and drawbacks may be noted. For example, where it is a mixture of butyraldehydes which are being separated, the n-butyraldehyde obtained from the second column of a two column process is likely to be more pure and contain fewer high-boiling components and less iso-butyraldehyde than the side draw taken from the first distillation column. It has therefore been proposed that the to connect the first and second distillation columns in series, where the bottoms of the first column are separated in a second column into a stream of high-boiling components and a pure, iso-butyraldehyde free, n-butyraldehyde stream, thereby achieving the same high n-butyraldehyde yield.

There are, however, significant drawbacks associated with the use of a two-step distillation process. One drawback is that a significant amount of the desired aldehyde product is lost due to its conversion into high-boiling components. This is a direct result of the high temperatures that are required to recover straight-chain aldehydes, such as n-butyraldehyde. For example, it has been estimated that approximately 1 to 2% by weight or more of n-butyraldehyde may be lost as a result of the in situ conversion to high-boiling components, which is a significant amount when the process is used on a commercial scale. Further, any straight-chain aldehyde taken from a side draw from the first distillation column typically contains some of the high-boiling components that are introduced into the column, which pass the side draw from which straight-chain aldehyde is obtained following addition to the column. It is also understood that the branched-chain aldehyde content in the first distillation column will increase and may sharply increase with every tray upwards from the bottom of the column, so it is necessary to add additional duty needs to the reboiler in order to achieve the desired branched-chain aldehyde content.

Additionally, in order to obtain straight-chain aldehydes in high yield, it is important to produce a concentrated stream of high-boiling components. The high-boiling components are much less volatile than straight-chain aldehydes and thus require an elevated temperature in the column bottoms. At elevated temperatures other reactions become important, such as further condensing of aldehydes or cracking of high-boiling components. Cracking of high-boiling components that are complexes or oligomers of branched-chain aldehydes may release branched-chain aldehydes back into the distillation column, which could then ultimately end up being present in the straight-chain aldehyde stream thereby undoing the effort taken to remove the branched-chain aldehydes. It is therefore paramount that the temperature in the second column remains relatively low, preferably the same temperature as in the first column. To achieve this, the pressure of the first column can be reduced or the concentration of high-boiling components can be limited by leaving a still significant amount of straight-chain aldehyde in the stream of high-boiling components.

Attempts to improve the distillation process and the separation of straight-chain and branched-chain aldehydes, such as n-butyraldehyde and iso-butyraldehyde, have focused on the addition of different components to aid distillation and minimise the formation of impurities. For example, a process in which water was added to a mixed butyraldehyde feed is disclosed in U.S. Pat. No. 5,227,544. The amount of water added to the butyraldehyde feed is said to be sufficient to hydrolyse the iso-butyraldehyde oligomers to the monomeric form during distillation, which reduces the amount of iso-butyraldehyde present in the final product and it also reduces the number of impurities formed when making 2-ethylhexanol. An alternative attempt to improve the distillation process and the separation of n-butyraldehyde and iso-butyraldehyde is disclosed in DE3320648, which describes the addition of a mono-carboxylic acid, such as butyric acid, that is intended to reduce the formation of high-boiling components in the distillation column. The mono-carboxylic acid is said to be formed in-situ by feeding air into the column. However, the addition of other components into distillation columns has been associated with drawbacks, such as the need to separate the additional components from the butyraldehyde. Water, for example, can be an unfavourable component, because it can cause the liquid to foam and render the trays ineffective or limit the capacity of the column below its intended capacity.

There therefore remains a need for a new and improved process for purifying an aldehyde mixture comprising separating a straight-chain aldehyde and a branched-chain aldehyde, which does not suffer from the drawbacks associated with the prior art. Specifically, there remains a need for an improved process for separating n-butyraldehyde from mixtures of n-butyraldehyde and iso-butyraldehyde which enable the desired n-butyraldehyde to be obtained at a purity in excess of at least 95%, at a purity of at least 98%, at a purity of at least 99% and preferably 100% purity. It has been found that the process of the present invention, which involves three-stages of separation, results in straight-chain aldehydes, such as n-butyraldehyde, that are obtained in both high yields and high purity. The process of the invention also avoids the formation of additional high-boiling components, which is a disadvantage associated with existing two-step distillation processes.

Thus, according to a first aspect of the invention, there is provided a process for the distillation of an aldehyde mixture comprising a straight-chain aldehyde and a branched-chain aldehyde wherein the process comprises:

i) supplying a feed comprising the aldehyde mixture to a first separation vessel;

ii) operating said first separation vessel at a first temperature and a first pressure such that separation occurs;

iii) recovering a first stream comprising the straight-chain aldehyde from said first separation vessel and supplying said first stream to a second separation vessel;

iv) operating said second separation vessel at a second temperature and a second pressure such that separation occurs;

v) recovering a product stream comprising the straight-chain aldehyde and a second stream comprising high-boiling components from said second separation vessel, and supplying said second stream to a third separation vessel;

vi) operating said third separation vessel at a third temperature and a third pressure such that separation occurs; and vii) recovering a third stream comprising the aldehyde mixture from said third separation vessel and reintroducing said third stream to the first separation vessel.

The aldehyde mixture used in the process of the present invention may be products obtained from a hydroformylation process. Examples of hydroformylation processes are described in U.S. Pat. Nos. 4,148,830, 4,247,486, 4,593,127 and 6,100,432. However, the distillation process of the present invention may be used to separate an aldehyde mixture produced by other hydroformylation processes or by other processes.

In one arrangement, the starting materials for the hydroformylation reaction may be an olefin or mixture of olefins. Examples of suitable olefins include ethylene, propylene, 1-butene, 2-butene (cis- or trans-) and isobutylene. The aldehydes obtained from the hydroformylation process will have one more carbon atom than that of the olefin starting material.

A catalyst is typically used in hydroformylation reactions. Any suitable catalyst may be used. Examples of suitable catalysts that may be used in hydroformylation reactions are described in U.S. Pat. No. 5,102,505. In one arrangement, the catalyst may be a rhodium catalyst which may optionally be used in combination with one or more ligands. The one or more ligand may be a phosphine or a phosphite. In one arrangement, the one or more ligand may be triphenylphosphine.

The ratio of straight chain to branch chain aldehydes present in the feed will generally depend on the process used for the production of the aldehydes.

In addition to the aldehydes, the feed may additionally include lighter-boiling components, heavier-boiling components or both lighter and heavier-boiling components. The amount of other components in the feed may be from about 0.1 to about 5% by weight, from about 0.2 to about 4% by weight, or from about 0.2 to about 3% by weight.

The process of the invention has the advantage that it may be carried out at lower cost and under more mild conditions than existing separation processes. Further, the process may enable a straight-chain aldehyde content of from about 98% to about 99.98%. Purities of from about 99%, or about 99.9% or even of 100% purity may be achieved.

The straight-chain aldehyde product stream may contain less than about 0.5% by weight of high-boiling components. Alternatively it may contain less than about 0.4%, 0.3%, 0.2%, or 0.1%, 0.05%, 0.02% or 0.01% by weight of high-boiling components.

Whatever the composition of the feed, it is fed to the first separation vessel. In one arrangement, the feed comprises straight-chain and branched-chain $C_{3-5}$ aldehydes. Thus the feed may comprise n- and iso-butyraldehydes, or n- and iso-valeraldehydes. In one arrangement, the feed may comprise a mixture of n- and iso-butyraldehyde.

The first separation vessel may be any suitable separation vessel. In one arrangement, the first separation vessel may be a distillation column, such as a tray column or a packed column. If the first separation vessel is a tray column, any suitable number of trays may be used. In one arrangement, the number of trays may be from about 40 to about 160, from about 50 to about 150, from about 60 to about 140, from about 70 to about 130, or from about 80 to about 120.

The feed may be supplied to any portion of the first separation vessel. In one arrangement, the feed may be supplied to a mid-portion of the first separation vessel, such as, for example at from about tray 5 to 100, or at from about tray 10 to 90. In this connection, the trays are numbered from the top of the column.

The first separation vessel may further comprise a reboiler, a condenser, or a reboiler and condenser, optionally the first separation vessel may further comprise a reflux drum, a reflux pump or a reflux drum and a reflux pump.

In order to facilitate separation, the first separation vessel is operated at any suitable temperature and pressure. The temperature and pressure will depend on the composition to be separated and the form of the first separation vessel. In one arrangement, the temperature of a lower portion of the first separation vessel may be from about 200° C. to about 65° C., from about 125° C. to about 85° C., from about 120° C. to about 90° C., from about 115° C. to about 95° C., or from about 110° C. to about 100° C. In one arrangement, the pressure of the first separation vessel may be from about 1.0 to about 2.4 bara, from about 1.2 to about 2.2 bara, or from about 1.4 to about 2.0 bara. However, it will be understood, that there will generally be a temperature and pressure profile in which the bottom of the reactor is warmer and have an increased pressure than the top of the column. Thus for example, in one arrangement, the first separation vessel may have a pressure at the top of about 1.5 bara and about 2.3 bara, a bottom temperature of about 104° C. and a top temperature in the region of about 73° C.

It will be understood that the first separation vessel operated such that the straight-chain aldehyde may be recovered along with the high-boiling components from the bottom of the first separation vessel. The lighter-boiling components, including iso-butyraldehyde, may be recovered from at or near the top of the first separation vessel.

The first stream, comprising the straight-chain aldehyde and the high-boiling components, is passed to the second separation vessel. In one arrangement, the first stream may be recovered from the bottom of the first separation vessel.

The second separation vessel may be any suitable separation vessel, which may be the same as or different from the first separation vessel. In one arrangement, the second separation vessel may be a distillation column, such as a tray column or a packed column. If the second separation vessel is a tray column, any suitable number of trays may be used. In one arrangement, the number of trays in the tray column may be from about 2 to about 100, from about 2 to about 50, from about 3 to about 25, from about 4 to about 20, from about 4 to about 15, from about 4 to about 10; of from 6 to 8 trays. In one arrangement, the number of trays in the second separation vessel may be less than the number of trays present in the first separation vessel.

The first stream may be supplied to any portion of the second separation vessel. In one arrangement, the first stream may be supplied to any suitable position. In one arrangement it may be provided to a mid-portion of the second separation vessel, such as a about trays 45 to 55 when the number of trays is from 2 to 100, at from about trays 20 to 30 when the number of trays is from about 2 to about 50, at from about trays 8 to 12 when the number of trays is from about 4 to about 15, or at from about 6 to 8, when the number of trays is from about 4 to about 10. In this connection, the trays are numbered from the top of the column. In one alternative arrangement, the first stream is supplied to the second separation vessel at a tray from 1 to 10 above the bottom of the column, from about 2 to 9 above the bottom of the column, from about 3 to 7 above the bottom of the column The second separation vessel may comprise a reboiler, a condenser, or a reboiler and condenser, optionally the second separation vessel may further comprise a reflux drum, a reflux pump or a reflux drum and a reflux pump. In arrangements wherein the second separation vessel is a tray column and it comprises a reboiler and condenser, the number of trays may be from 2 to 100, from about 2 to about 50, from about 3 to about 25, from about 4 to about 20, from about 4 to about 15, from about 4 to about 10, of from 6 to 8 trays.

Similarly, in such arrangements, the first stream may be supplied any suitable position. In one arrangement, it may be supplied to a mid-portion of the second separation vessel, such as at from about trays 40 to 55 when the number of trays is from 2 to 100, or at from about trays 42 to 50, or at from about trays 45 to 48. such as a about trays 45 to 55 when the number of trays is from 2 to 100, at from about trays 20 to 30 when the number of trays is from about 2 to about 50, at from about trays 8 to 12 when the number of trays is from about 4 to about 15, or at from about 6 to 8, when the number of trays is from about 4 to about 10. In this connection, the trays are numbered from the top of the column.

In order to facilitate separation, the second separation vessel is operated at any suitable temperature and pressure. The temperature and pressure will depend on the composition to be separated and the form of the second separation vessel. In one arrangement, the temperature of a lower portion of the second separation vessel may be from about 200° C. to about 65° C., from about 125° C. to about 85° C., from about 120° C. to about 90° C., from about 115° C. to about 95° C., or from about 110° C. to about 100° C. The temperature of the upper portion of the second separation vessel may be lower than that of the first separation vessel, such that the formation of high-boiling components and/or cracking of high-boiling components to form straight-chain and branched-chain aldehydes is minimised. In one arrangement, the pressure of the second separation vessel may be from about 1.0 to about 2.4 bara, from about 1.2 to about 2.2 bara, or from about 1.4 to about 2.0 bara. However, it will be understood, that there will generally be a temperature and pressure profile in which the bottom of the reactor is warmer and have an increased pressure at the bottom of the separation vessel. Thus for example, in one arrangement, the second separation vessel may have a pressure at the top of about 1.5 bara and about 2.3 bara, a bottom temperature of about 104° C. and a top temperature in the region of about 70° C. to about 100° C.

It will be understood that the second separation vessel is operated such that the straight-chain aldehydes may be separated from the high-boiling components. The straight-chain aldehydes may be recovered from the top of the second separation vessel as a product stream. The high-boiling components may be recovered from the bottom of the second separation vessel.

The second stream, comprising the high-boiling components, obtained from the second separation vessel is passed to the third separation vessel. In one arrangement, the second stream may be taken from the bottom of the second separation vessel.

The third separation vessel may be any suitable separation vessel, which may be the same as or different from the first separation vessel and/or the second separation vessel. In one arrangement, the third separation vessel may be a distillation column, such as a tray column or a packed column. If the separation vessel is a tray column, any suitable number of trays may be used. In one arrangement, the number of trays in the tray column may be from about 2 to about 100, from about 2 to about 50, from about 3 to about 25, from about 4 to about 20, from about 4 to about 15, or from about 4 to about 10. In one arrangement, the number of trays in the tray column of the third separation vessel may be less than the number of trays present in the first separation vessel. In one arrangement, where the first, second and third separation vessels are tray columns, the number of trays in the second and third separation vessels may be less than the number of trays present in the first separation vessel.

The second stream may be supplied to any portion of the third separation vessel. In one arrangement, the second stream may be supplied to a mid-portion of the third separation vessel, such as at from about trays 45 to 55 when the number of trays is from about 2 to about 100, at from about trays 20 to 30 when the number of trays is from about 2 to about 50, at from about trays 10 to 15 when the number of trays is from about 3 to about 25 or the number of trays is from 4 to about 20, or at from about trays 8 to 12 when the number of trays is from about 4 to about 15, or from about 6 to 8 when the number of trays is from about 4 to about 10. In this connection, the trays are numbered from the top of the column.

The third separation vessel may comprise a reboiler, a condenser, or a reboiler and condenser, optionally the third separation vessel may further comprise a reflux drum, a reflux pump or a reflux drum and a reflux pump. In arrangements wherein the third separation vessel is a tray column and it comprises a reboiler and condenser, the number of trays may be from about 1 to about 100, from about 2 to about 50, from about 2 to about 25, from about 2 to about 20, from about 4 to about 15, or from about 5 to about 10. The second stream may be supplied to any suitable position. In one arrangement it may be supplied to a mid-portion of the third separation vessel, such as at from about trays 7 to 13, when the number of trays is from about 2 to about 20, or at from about trays 8 to 10, when the number of trays is from about 4 to about 15, or at from trays 6 to 8, when the number of trays is from about 5 to about 10. In this connection, the trays are numbered from the top of the column. In one alternative arrangement, the second stream is supplied to the second separation vessel at a tray from 1 to 10 above the bottom of the column, from about 2 to 9 above the bottom of the column, from about 3 to 7 above the bottom of the column.

In one arrangement, the third separation vessel may be a partial vaporiser, such that the separation vessel does not comprise any trays and it does not comprise a condenser. The partial vaporiser may be a single kettle type reboiler or vaporiser, or a vessel with an external reboiler.

In order to facilitate separation, the third separation vessel is operated at any suitable temperature and pressure. The temperature and pressure will depend on the composition to be separated and the form of the third separation vessel. In one arrangement, the temperature of a lower portion of the third separation vessel may be from about 200° C. to about 65° C., 125° C. to about 85° C., or from about 120° C. to about 90° C., or from about 115° C. to about 95° C., from about 110° C. to about 100° C. In one arrangement, the pressure of the third separation vessel may be from about 1.0 to about 2.4 bara, from about 1.2 to about 2.2 bara, or from about 1.4 to about 2.0 bara. However, it will be understood, that there will generally be a temperature and pressure profile in which the bottom of the reactor is warmer and have an increased pressure at the bottom of the separation vessel. Thus for example, in one arrangement, the third separation vessel may have a pressure at the top of about 1.5 bara and about 2.3 bara, a bottom temperature of about 130 to 131° C. and a top temperature in the region of about 70° C. to about 100° C.

It will also by understood that the third separation vessel operates such that the separation conditions may allow the decomposition of high-boiling components and their reversion to straight-chain and/or or branched-chain aldehydes that can be recovered as a third stream, which may be removed from the top of the third reaction vessel. Any remaining high-boiling components are removed from the bottom of the third separation vessel.

The three-stage process of the present invention is less sensitive towards operating conditions than existing prior art processes, so the third separation vessel may be operated at harsher conditions, such as elevated temperatures and/or pressures than were usable in prior art processes.

The stream comprising straight-chain and branched-chain aldehydes recovered from the third separation vessel may be recycled to the first separation vessel. In one arrangement, the third stream may be may be taken as the top product of the third separation vessel. It will be readily apparent that the tray at which the third stream may be recycled and supplied to the first separation vessel can be optimised depending on the conditions that are used. The operation of the third separation vessel may include the injection of water into the third column in a process similar to that described in U.S. Pat. No. 5,227,544.

It will be understood that the temperatures and pressures indicated above are only indicative. Each separation vessel has a different task and duty and the operation conditions will be selected appropriately. In summary, the role of the first separation vessel is to remove the branched-chain aldehydes and lights from the aldehyde feed stream. The stream from the bottom of this separation vessel which has a reduced branched-chain aldehyde content is treated in the second separation vessel. A portion of this feed is removed from the second separation column as overhead from the second separation vessel leaving a mixture of heavy, higher-boiling, components and straight-chain aldehydes. These components are separated in the third separation vessel. This third separation vessel may be operated at a temperature which is higher than that used in the second separation vessel as this may enable some of the undesirable heavies to be reverted to the branched- and/or straight-chain aldehydes which can then be recycled to the first separation vessel to enable further separation.

The first, second and third separation vessels may be any suitable separation vessel, such as tray columns or packed columns. In one arrangement, the first, second and third separation vessels may be the same or different, where the separation vessels are different it will be understood that any combination of separation vessels is permitted. For example, the first, second and third separation vessels may be tray columns, or the first and second separation vessels may be tray columns and the third vessel a packed column, or the first and third vessels may be tray columns and the second vessel may be a packed column.

The type of separation vessels used and the aldehydes being separated may impact on the separation conditions that are used. Accordingly, it will be understood that combinations of separation conditions, such as temperatures and pressures, the form of the separation vessel, such as tray columns and the number of trays and the portion of the vessel to which streams are introduced to the tray columns, set out above are also envisaged. For example, it will be understood that mixtures of n- and iso-butyraldehyde may be separated by three separation vessels, wherein each separation vessel is a tray column, and the first separation vessel comprises from about 40 to about 160 trays, the feed is supplied to a mid-portion of the first separation vessel, at from about tray 90 to 110, and the temperature and pressure of the first separation vessel is from about 115° C. to about 95° C. and from about 1.2 to about 2.4 bara, wherein the second separation vessel comprises from about 2 to about 50 trays, the first stream from the first separation vessel is supplied to a mid-portion of the second separation vessel, at from about trays 20 to 30, and the temperature and pressure of the second separation vessel is from about 110° C. to about 100° C. and from about 1.4 to about 2.2 bara, and wherein the third separation vessel comprises from about 3 to about 25 trays, the second stream from the second separation vessel is supplied to a mid-portion of the third separation vessel, at from about trays 10 to 15, and the temperature and pressure of the second separation vessel is from about 120° C. to about 90° C. and from about 1.0 to about 2.2 bara. It will be understood that other similar combinations of separation conditions, such as temperatures and pressures, the form of the separation vessel, such as tray columns and the number of trays and the portion of the vessel in which streams are introduced to the tray columns, are also envisaged. In this connection, the trays are numbered from the top of the column.

In one arrangement in which the first, second and/or third separation vessels are columns, any suitable size column may be used. In arrangements in which the first, second and third separation vessels are columns, the diameter of the first column may be greater than that of the second column and the diameter of the second column may be greater than that of the third column. It will be understood that the diameters of each of the columns selected may depend on the ratio of n- to iso-aldehyde in the feed stream, and the desired ratio of n- to iso-aldehyde in the stream removed from the top of the first separation vessel, the size of the third stream and the iso-aldehyde content of the third stream.

The present invention will now be described, by way of example, with reference to the accompanying figures in which.

For the avoidance of doubt, these figures are intended only as an aid to understanding the invention and are not intended to be construed as limiting the scope of the invention with regard to the precise arrangement of the components illustrated or the positioning thereof, the shape of the vessels or any of the ancillary features. It will be understood by those skilled in the art that the drawings are diagrammatic and that further items of equipment such as feedstock drums, pumps, vacuum pumps, compressors, gas recycling compressors, temperature sensors, pressure sensors, pressure relief valves, control valves, flow controllers, level controllers, holding tanks, storage tanks and the like may be required in a commercial plant. Provision of such ancillary equipment forms no part of the present invention and is in accordance with conventional chemical engineering practice.

Figure 1:
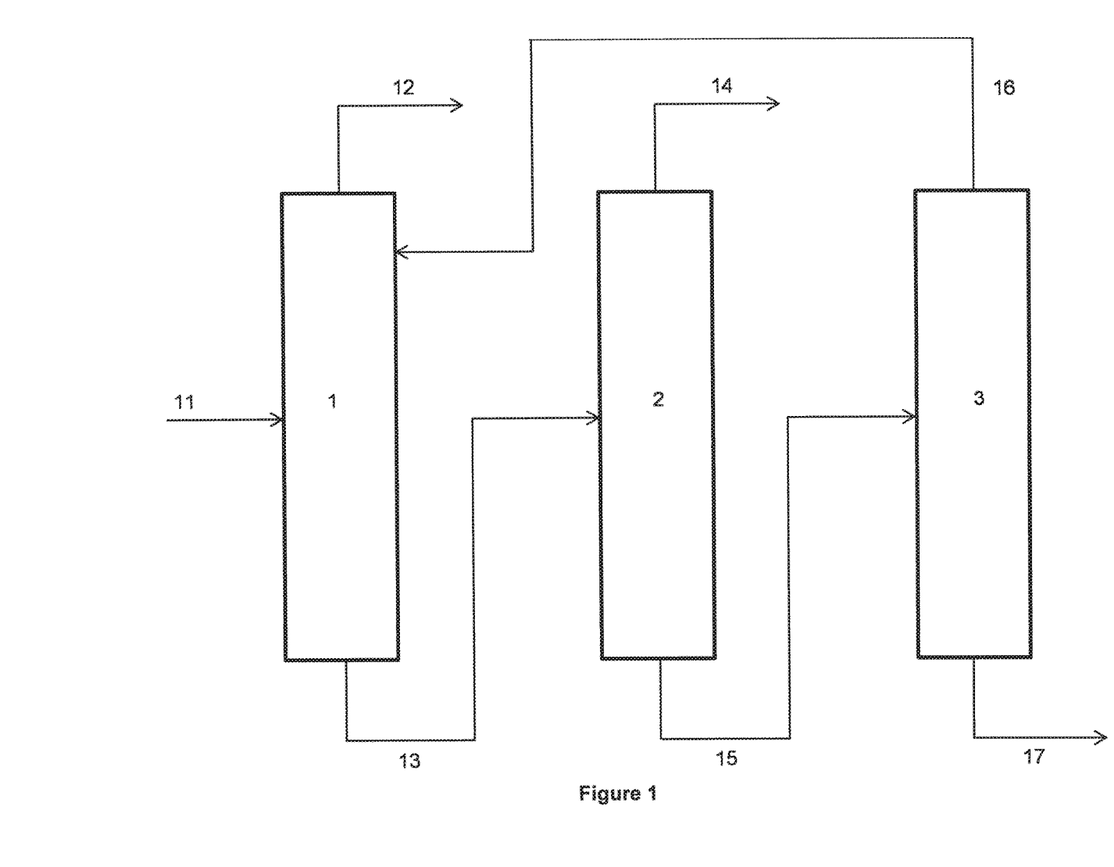
FIG. 1 is a schematic diagram of the process of a first aspect of the present invention.

As illustrated in FIG. 1, a feed stream comprising n-butyraldehyde, iso-butyraldehyde and high-boiling components is fed through line 11 to a first separation zone 1, where iso-butyraldehyde is separated from n-butyraldehyde and high-boiling components at elevated temperature and pressure. The first separation zone may comprise a tray column, and optionally a reboiler, a condenser, or a reboiler and condenser, a reflux drum, a reflux pump or a reflux drum and a reflux pump (not shown). The iso-butyraldehyde, which may include a small amount of n-butyraldehyde, is recovered by line 12.

A first stream comprising a mixture of n-butyraldehyde and high-boiling components is recovered from the first separation zone in line 13. The first stream is passed to a second separation zone 2, where n-butyraldehyde is separated from the high-boiling components at elevated temperature and pressure. The second separation zone may comprise a tray column, and optionally a reboiler, a condenser, or a reboiler and condenser, a reflux drum, a reflux pump or a reflux drum and a reflux pump (not shown). The n-butyraldehyde is recovered by line 14.

A second stream comprising dilute high-boiling components is recovered from the second separation zone by line 15. The second stream is passed to a third separation zone 3, where the high-boiling components are concentrated at elevated temperature and pressure. The third separation zone may comprise a tray column, and optionally a reboiler, a condenser, or a reboiler and condenser, a reflux drum, a reflux pump or a reflux drum and a reflux pump (not shown). The elevated temperature and pressure of the third separation zone allow some n-butyraldehyde and/or iso-butyraldehyde to be formed by decomposition of high-boiling components. The high-boiling components are concentrated and recovered from the third separation zone in line 17.

The aldehyde mixture formed in the third separation zone is recovered and reintroduced into the first separation zone in line 16.

Figure 2:
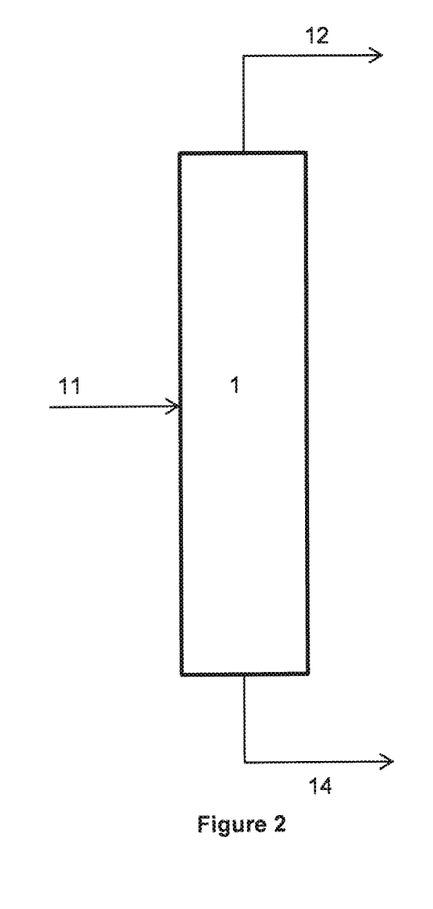
FIG. 2 is a schematic diagram of a comparative process comprising a single separation vessel.

An example of a single column separation is set out in FIG. 2, wherein a feed stream comprising n-butyraldehyde, iso-butyraldehyde and high-boiling components is fed through line 11 to a first separation zone 1. The feed stream is separated into n-butyraldehyde and iso-butyraldehyde at elevated temperature and pressure. The iso-butyraldehyde is recovered in line 12 and the n-butyraldehyde is recovered in line 14. Heavies in the feed that do not decompose and/or any heavies formed in the separation column will exit the column with the n-butyraldehyde.

Figure 3:
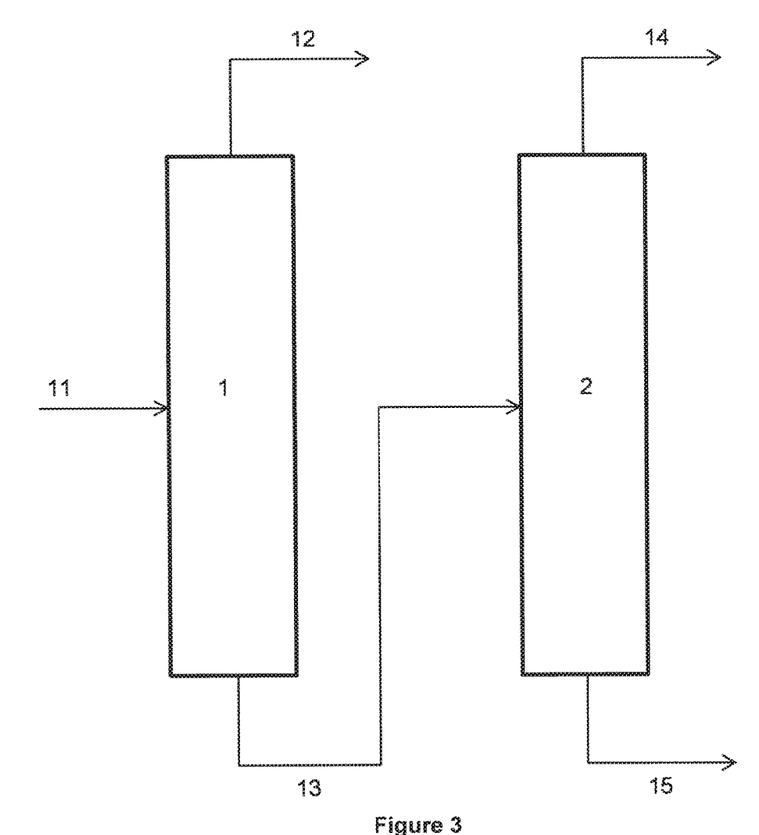
FIG. 3 is a schematic diagram of a comparative process comprising two separation vessels.

An example of a two-step separation process is set out in FIG. 3, wherein a feed stream comprising n-butyraldehyde, iso-butyraldehyde and high-boiling components is fed through line 11 to a first separation zone 1. The first separation zone 1 and the second separation zone 2 are connected in series by line 13.

The iso-butyraldehyde is separated from n-butyraldehyde and high-boiling components in the first separation zone, and recovered by line 12. The n-butyraldehyde and high-boiling components are recovered from the first separation zone and fed into the second separation zone 2 by line 13, wherein the n-butyraldehyde is separated from the high-boiling components. The n-butyraldehyde is recovered by line 14, and the high-boiling components are recovered by line 15.

Figure 4:
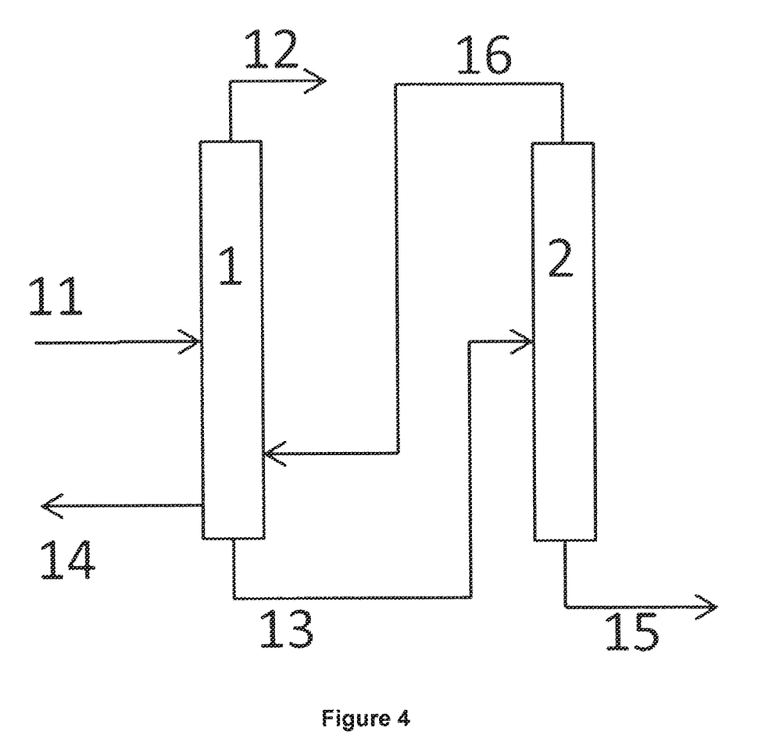
FIG. 4 is a schematic diagram of a comparative process comprising two separation vessels, and a recycled stream from the second separation vessel.

A further example of a two-step separation process is set out in FIG. 4, wherein a feed stream comprising n-butyraldehyde, iso-butyraldehyde and high-boiling components is fed through line 11 to a first separation zone 1. The first separation zone 1 and the second separation zone 2 are connected in series by line 13. A side draw of n-butyraldehyde is obtained from the first separation zone 1 in line 14.

The iso-butyraldehyde is separated from n-butyraldehyde and high-boiling components in the first separation zone, and recovered by line 12. The n-butyraldehyde and high-boiling components are recovered from the first separation zone are fed into the second separation zone 2 by line 13, wherein the n-butyraldehyde is separated from the high-boiling components. The high-boiling components are recovered by line 15 and the n-butyraldehyde is recovered and recycled to the first separation zone by line 16. The n-butyraldehyde obtained from the second separation zone 2 may be recovered directly into the first separation zone by line 16 or it may be introduced to the feed stream 11 before being recovered into the first separation zone, not shown.

As the iso-butyraldehyde concentration in the bottom trays sharply increases with every tray above the sump, to achieve a desired iso-butyraldehyde concentration in the n-butyraldehyde side draw the iso-butyraldehyde concentration at the bottom of the column needs to be about half that of the concentration which is desired. In order to achieve such a low iso-butyraldehyde concentration, in a column with the same number of trays, additional reboiler and condenser duties are typically required.

The present invention will now be described by way of example with reference to the accompanying Examples and Comparative Examples which have been generated using Simulation Sciences Inc Pro/II 8.2 modelling software available from Schneider Electric Software using known or readily determined physical properties.

The formation of high-boiling components and the presence of a reverse reaction in the following examples are not intended to represent actual reactions. These are present to simulate cracking of heavies. High-boiling components are generally thought to be the product of condensation reactions, such as aldol condensation, Tishchenko-type or Cannizzaro-type reactions, leading to multiples of $C_4$, e.g. $C_8$, $C_{12}$ and $C_{16}$ molecules with various numbers of oxygen atoms. These reactions are described in U.S. Pat. Nos. 5,841,002 and 6,193,872.

The reverse reaction is assumed to take place at elevated temperatures. In Comparative Examples 5 and 6 and Example 7, the reverse reactions take place in the column that operates with a bottoms temperature of 131° C. The first column, or butyraldehyde isomer column, requires requires the largest reboiler duty. It is assumed that the formation of high-boiling components takes place in this column as it will have the largest inventory of iso-butyraldehyde. However, high-boiling components may also be formed in the second and third columns, but this has been ignored for the purposes of the examples because it does not impact on the efficiency of iso-butyraldehyde removal from n-butyraldehyde, even though it does impact on the n-butyraldehyde yield.

Comparative Examples 3 and 6 show that a significantly higher concentration of $C_8$ high-boiling components (Tishchenko product of normal and iso-butyraldehyde) and ethyl-isopentenal (aldol condensation product of normal- or iso-butyraldehyde) present in the n-butyraldehyde product stream. This is mainly due to the fact that all high-boiling components are typically fed into the first column above the side draw and it is necessary for them to pass the side draw in order to be separated from the n-butyraldehyde product stream. Accordingly, it is inevitable that some high-boiling components will be present on the tray from which the n-butyraldehyde side draw is taken.

COMPARATIVE EXAMPLE 1

A single column separation vessel, as shown in FIG. 2, is used to separate a feed stream of 27,764 kg/h containing 3.22 mol % iso-butyraldehyde, 96.77 mol % n-butyraldehyde, 101 ppm mol trimer and 28 ppm mol 2-ethyl hexenal. To simulate the formation of various high-boiling components in the butyraldehyde isomer column, 0.5% of n-butyraldehyde is converted to a trimer, 0.5% of n-butyraldehyde is reacted with iso-butyraldehyde to form iso-butylbutyrate (via the Tishchenko reaction), 0.5% of n-butyraldehyde is reacted with iso-butyraldehyde to form ethyl-isopentenal (via an aldol condensation reaction). prior to entering the column. The feed stream is fed to the butyraldehyde isomer column at tray 40 when counted from the top of the column. The column is simulated using 80 theoretical trays, a reboiler and a condenser. The column is operated at 1.5 bara at the top and 2.3 bara at the bottom. The condensate obtained in the top condenser is decanted to remove water prior to returning to the column as reflux. The butyraldehyde isomer column is operated such that the iso-butyraldehyde obtained by overhead contains 0.06 mol % n-butyraldehyde, and the bottom product n-butyraldehyde contains 0.07 mol % iso-butyraldehyde. The temperature in the top of the column before the condenser is approximately 73° C. and the temperature in the bottom is approximately 103.5° C.

Comparative Example 1 requires a low reboiler duty, but any high-boiling components that are made in thus butyraldehyde isomer column are not separated from the n-butyraldehyde product stream.

COMPARATIVE EXAMPLE 2

A two-step separation process comprising two columns connected in series without recycle, as shown in FIG. 3, is used to refine the same feed as that used in Comparative Example 1 (including trimer, butyl butyrate, and ethyl-isopentenal). The butyraldehyde isomer column is identical to the column in Comparative Example 1 and operated to achieve the same iso-butyraldehyde and n-butyraldehyde specifications in top and bottom draw. The bottoms draw is sent to a second column. The second column contains 8 theoretical trays, a reflux ratio set at 0.25 mol/mol, and a reboiler. In addition, it contains a condenser cooling to the bubble temperature. In thermodynamics, the bubble point is the temperature, at a given pressure, where the first bubble of vapour is formed when heating a liquid consisting of two or more components. Given that vapour will probably have a different composition than the liquid, the bubble point, along with the dew point, at different compositions are useful data when designing distillation systems. The pressure was set at 1.5 bara in the top of the column and a pressure gradient resulting in a pressure of 2.3 bara in the bottom. In the second column, which operates at 1.5 bara in the top and has a negligible pressure gradient the stream of high-boiling components is concentrated such that the bottoms temperature is 131° C. Pure n-butyraldehyde product is obtained as a liquid from the top of the second column and a concentrated stream of high-boiling components is obtained from the bottom.

When compared with Example 1, there is an observable reduction in the number of high-boiling components in the n-butyraldehyde obtained from the second column as illustrated in Table 1.

COMPARATIVE EXAMPLE 3

A two-step separation process comprising two columns connected in series with recycle, as shown in FIG. 4, is used to refine the same feed as that used in Comparative Example 1 (including trimer, butyl butyrate, and ethyl-isopentenal) was used. The butyraldehyde isomer column is operated such that the iso-butyraldehyde obtained overhead contains 0.06 mol % n-butyraldehyde, a n-butyraldehyde rich vapour stream is taken as a side draw at tray 79 (one tray above the sump) containing 0.07 mol % iso-butyraldehyde. A bottoms draw containing most of the high-boiling components is obtained and send to a second column. The second column contains 8 theoretical trays, a reboiler, a condenser cooling to the bubble temperature and a reflux ratio set at 0.25 mol/mol. The pressure was set at 1.5 bara. In the second column the stream of high-boiling components is concentrated such that the bottoms temperature is 131° C. The overhead of the second column containing primarily n-butyraldehyde is returned to the first column as a liquid, and inserted in tray 70 when counted from the top of the column.

Comparative Example 3 shows an increase in the reboiler duty. This is mainly due to the fact that n-butyraldehyde is taken as a side draw above the sump.

EXAMPLE 4

A three-step separation process according to the present invention, and as shown in FIG. 1, utilises the same set-up as that of Comparative Example 2, except the second column is operated to produce a bottoms temperature of 104° C., and a concentrated stream of high-boiling components obtained from the second column bottoms is sent to a third column is used to refine the same feed as that used in Comparative Example 1. The third column contains 8 theoretical trays, with a condenser cooling to the bubble temperature and a reflux ratio set at 0.25 mol/mol, and a reboiler. The pressure was set at 1.5 bara throughout the column. In the third column the stream of high-boiling components is separated such that the bottoms temperature is 131° C. The overheads obtained from the third column, containing primarily butyraldehyde, is returned to the first column as a liquid, and inserted on tray 70 when counted from the top of the column

COMPARATIVE EXAMPLE 5

A two-step separation process with the inclusion of the reverse decomposition of 50% of the butylbutyrate present in the feed to the second column to form iso-butyraldehyde and n-butyraldehyde prior to entering the second column is used to refine the same feed as that used in Comparative Example 1. This is to simulate iso-butyraldehyde formation due to the increased temperature in the second column. The first column is operated identical to Comparative Example 2, i.e. aiming for the same iso-butyraldehyde concentration in the n-butyraldehyde stream.

All of the iso-butyraldehyde formed by the reverse reaction leaves with the n-butyraldehyde product stream, which is in contrast to Comparative Example 2 (see Table 1).

COMPARATIVE EXAMPLE 6

A two-step separation process has a set-up that is the same as that of Comparative Example 3, and as shown in FIG. 4, is used to refine the same feed as that used in Comparative Example 1. The reverse reaction is the same as that set out in Comparative Example 5, i.e. 50% of butylbutyrate is converted to normal- and iso-butyraldehyde in the feed to the second column. The first column is now operated identical to Comparative Example 3, i.e. aiming for the same iso-butyraldehyde concentration in the bottom stream.

EXAMPLE 7

A three-step separation process including a reverse reaction that is set-up in the same way as that of Example 4, and shown in FIG. 1 is used to refine the same feed as that used in Comparative Example 1. The reverse reaction is the same as that which is set out in Comparative Example 5 with the exception that 50% of butylbutyrate is converted to normal- and iso-butyraldehyde in the feed to the third column rather than to the second column. The first column is operated identical to Comparative Example 4, i.e. aiming for the same iso-butyraldehyde concentration in the bottom stream. The overheads obtained from the third column, containing primarily butyraldehyde, is returned to the first column as a liquid, and inserted on tray 35 the recycle now contains more iso-butyraldehyde than in Example 4 and it is therefore recycled to a higher position in the column.

The Examples show that the three-stage separation process according to the invention yields n-butyraldehyde that has the lowest concentrations of iso-butyraldehyde and iso-butylbutyrate and ethyl-isopentenal when compared with existing processes, even in the presence of a reverse reaction. The Examples also show that the use of a three-stage separation process advantageously requires a smaller reboiler duty that that which is required by the prior art processes, and existing two-stage processes.

The results of the examples and comparative examples are set out in Table 1

TABLE 1

|  |  | Comp. Eg 1 | Comp. Eg 2 | Comp. Eg 3 | Eg 4 | Comp. Eg 5 | Comp. Eg 6 | Eg 7 |
| --- | --- | --- | --- | --- | --- | --- | --- | --- |
| Reboiler duty first column | MW | 11.92 | 11.92 | 16.44 | 11.95 | 11.92 | 18.38 | 12.22 |
| Reboiler duty second column | MW | n/a | 3.64 | 1.08 | 3.63 | 3.69 | 1.13 | 3.64 |
| Reboiler duty third column | MW | n/a | n/a | n/a | 0.074 | n/a | n/a | 0.12 |
| sum reboiler duties | MW | 11.92 | 15.56 | 17.52 | 15.65 | 15.61 | 19.51 | 15.98 |
| n-butyraldehyde Yield | mol % | 98.5 | 98.0 | 98.0 | 98.0 | 98.3 | 98.3 | 98.3 |
| iso-butyraldehyde in stream 14 | ppm wt | 700 | 700 | 700 | 700 | 3225 | 702 | 700 |
| iso-butylbutyrate in stream 14 | ppm wt | 9900 | 30 | 209 | 4 | 16 | 190 | 4 |
| ethyl isopentene hexenal in stream 14 | ppm wt | 8666 | 0.1 | 88 | 0 | 0.1 | 79 | 0 |
| Trimer in stream 14 | ppm wt | 5262 | 0.0 | 0.3 | 0 | 0 | 0.3 | 0.0 |

It will be understood that stream 14 is the product stream with purified normal-butyraldehyde.

COMPARATIVE EXAMPLE 8 (C5 EXAMPLE ANALOGUE OF EXAMPLE 5)

A two-step separation process is used for the separation of 2-methylbutyraldehyde and valeraldehyde and is therefore a C5 analogue to Example 5. A feed of 9,121.5 kg/h containing 49.55 wt % 2-methylbutyraldehyde, 49.55 wt % valeraldehyde, 0.17 wt % of isopentylvalerate, 0.12 wt % C5 Trimer, and minor fractions of C5 paraffins is fed to an isomer column. To simulate the formation of various high-boiling components in the isomer column, 0.5 wt % of n-valeraldehyde is reacted with 2-methylbutyraldehyde to form C5 Trimer, 0.5 wt % of valeraldehyde is reacted with 2-methylbutyraldehyde to form a $C_{10}$ acrolein and another 0.5 wt % of valeraldehyde is reacted 2-methylbutyraldehyde to form isopentylvalerate prior to entering the column. The column is simulated using 80 theoretical trays with the feed coming in at tray 37 from the top. The column is operated such that overhead product contains 0.2 wt % valeraldehyde. The column is operated at 1.2 bara at the top and 2.0 bara at the bottom and 1000 ppmw of 2-methylbutyraldehyde in the bottom product. The temperature in the top of the column is approximately 96° C. and about 127° C. in the bottom. The bottom product is fed to a second column to remove heavies from the valeraldehyde product. The column is simulated using 5 theoretical trays with the feed entering at tray 4 from the top. The pressure in the top of the column is 1.1 bara. The column is operated to give a concentration of 10 wt % of valeraldehyde in the bottom product. A reflux ratio of 1.0 is used. The top product is drawn as a liquid. At these conditions the temperature in the top is 106° C. in the top and 170° C. in the bottom. The high temperature in the bottom may generate decomposition reactions in the bottom. To simulate the decomposition of heavy components in the bottom 50% of the isopentylvalerate is converted back to 2-methylbutyraldehyde and valeraldehyde prior to entering the column.

COMPARATIVE EXAMPLE 9 (C5 EXAMPLE ANALOGUE TO EXAMPLE 6)

A two-step separation process has a set-up that is the same as that of Comparative Example 6, and as shown in FIG. 4. As in Example 8 the isomer column is operated to give 0.2 wt % of valeraldehyde in the top product. A vapour side draw of n-valerlaldehyde is taken from tray 78 from the top of the isomer column. The isomer column is operated to give approximately 1000 ppmw of 2-methylbutyraldehyde in the side draw. The flowrate taken from the bottom of the column is 2831 kg/h. The second column is operated in the same way as in Example 8. The overhead product of the second column is returned to the isomer column at tray 60 from the top. The reverse reaction is the same as that set out in Comparative Example 8, i.e. 50% of isopentylvalerate is converted to 2-methylbutyraldehyde and n-valeraldehyde in the feed to the second column.

EXAMPLE 10 (C5 EXAMPLE ANALOGUE TO EXAMPLE 7)

A three-step separation process has a reverse reaction which is the same as the set-up of Example 4, and shown in FIG. 1. The reverse reaction is the same as that which is set out in Comparative Examples 8 and 9, with the exception that 50% of isopentylvalerate is converted to 2-methylbutyraldehyde and valeraldehyde in the feed to the third column. The first column is operated to give 0.2 wt % of valeraldehyde in the top product and about 970 ppm wt in the bottom product, i.e. aiming for 1000 ppm wt of 2-methylbutyraldehyde in the product n-valerlaldehyde obtained from the top of the second column. The overheads obtained from the third column, containing primarily aldehydes, is returned to the first column as a liquid, and inserted on tray 46 the recycle now contains more 2-methylbutyraldehyde than in Example 9 and it is therefore recycled to a higher position in the column.

The Examples show that the three-stage separation process according to the invention yields n-butyraldehyde that has the lowest concentrations of iso-butyraldehyde and iso-butylbutyrate and ethyl-isopentenal when compared with existing processes, even in the presence of a reverse reaction. The Examples also show that the use of a three-stage separation process advantageously requires a smaller reboiler duty that that which is required by the prior art processes, and existing two-stage processes.

The results of the Example 10 and Comparative examples 8 and 9 are set out in Table 2

TABLE 2

|  |  | Example 8 | Example 9 | Example 10 |
|---|---|---|---|---|
| Reboiler Duty 1$^{st}$ Column | MW | 4.8236 | 6.1586 | 4.9309 |
| Reboiler Duty 2$^{nd}$ Column | MW | 0.8540 | 0.5126 | 0.9337 |
| Reboiler Duty 3$^{rd}$ Column | MW | n/a | n/a | 0.0389 |
| Sum Reboiler Duties | MW | 5.6776 | 6.6712 | 5.9035 |
| n-valeraldehyde yield | mol % | 98.21 | 98.21 | 98.22 |
| 2-methylbutyraldehyde in stream 14 | ppm wt | 3565 | 1005 | 1004 |
| isopentylvalerate in stream 14 | ppm wt | 74.6 | 47 | 9 |
| acrolein in stream 14 | ppm wt | 0.0 | 4.4 | 0.0 |
| C5Trimer in stream 14 | ppm wt | 0.0 | 0.3 | 0.0 |

The invention claimed is:

1. A process for the distillation of an aldehyde mixture comprising a straight-chain aldehyde and a branched-chain aldehyde wherein the process comprises:
   i) supplying a feed comprising the aldehyde mixture to a first separation vessel;
   ii) operating said first separation vessel at a first temperature and a first pressure such that separation occurs;
   iii) recovering a first stream comprising the straight-chain aldehyde from said first separation vessel and supplying said first stream to a second separation vessel;
   iv) operating said second separation vessel at a second temperature and a second pressure such that separation occurs;
   v) recovering a product stream comprising the straight-chain aldehyde and a second stream comprising high-boiling components from said second separation vessel, and supplying said second stream to a third separation vessel;
   vi) operating said third separation vessel at a third temperature and a third pressure such that separation occurs; and
   vii) recovering a third stream comprising the aldehyde mixture from said third separation vessel and reintroducing said third stream to the first separation vessel.

2. The process according to claim 1, wherein the feed comprises: straight-chain and branched-chain $C_4$ aldehydes; or straight-chain and branched-chain $C_5$ aldehydes.

3. The process according to claim 1, wherein the first separation vessel, the second separation vessel, or the third separation vessel are each individually a distillation column.

4. The process according to claim 1, wherein the temperature of a lower portion of any one of the first, second, or third separation vessels is from about 200° C. to about 65° C., from about 125° C. to about 85° C., from about 120° C. to about 90° C., from about 115° C. to about 95° C., or from about 110° C. to about 100° C.

5. The process according to claim 1, wherein the pressure of any one of the first, second, or third separation vessels is selected from about 1.0 to about 2.4 bara, from about 1.2 to about 2.2 bara, or from about 1.4 to about 2.0 bara.

6. The process according to claim 1, wherein the first separation vessel is a tray column, optionally wherein the number of trays in the tray column is from about 40 to about 160; or from about 50 to about 150; or from about 60 to about 140; or from about 70 to about 130; or from about 80 to about 120.

7. The process according to claim 6, wherein the feed is supplied to the first separation vessel at from about trays 5 to 100, or at from about trays 10 to 90 as counted from the top of the column.

8. The process according to claim 1, wherein the second separation vessel is a tray column, optionally wherein the number of trays in the tray column is from about 2 to about 100, from about 2 to about 50, from about 3 to about 25, from about 4 to about 20, from about 4 to about 15, or from about 4 to about 10.

9. The process according to claim 8, wherein the first stream is supplied to the second separation vessel at a tray from 1 to 10 above the bottom of the column, from about 2 to 9 above the bottom of the column, or from about 3 to 7 above the bottom of the column.

10. The process according to claim 1, wherein the third separation vessel is a tray column, wherein the number of trays in the tray column is from about 2 to about 100, from about 2 to about 50, from about 3 to about 25, from about 4 to about 20, from about 4 to about 15, or from about 4 to about 10.

11. The process according to claim 10, wherein the second stream is supplied to the second separation vessel at a tray from 1 to 10 above the bottom of the column, from about 2 to 9 above the bottom of the column, or from about 3 to 7 above the bottom of the column.

12. The process according to claim 1, wherein the first, second, or third separation vessels each individually further comprise a reboiler, a condenser, a reboiler and condenser, a reflux drum, a reflux pump, or a reflux drum and a reflux pump.

13. The process according to claim 1, wherein the first and second separation vessels are tray columns, and the number of trays in the second separation vessel is less than the number of trays present in the first separation vessel.

14. The process according to claim 1, wherein the first and third separation vessels are tray columns, and the number of trays in the third separation vessel is less than the number of trays present in the first separation vessel.

15. The process according to claim 1, wherein the first, second, and third separation vessels are tray columns, and the number of trays in the second and third separation vessels is less than the number of trays present in the first separation vessel.

16. The process according to claim 1, wherein the third separation vessel is a partial vaporiser, wherein the vessel does not comprise any trays and it does not comprise a condenser, and optionally the partial vaporiser is selected from a single kettle-type reboiler or vaporiser, or a vessel with an external reboiler.

17. The process according to claim 3, wherein the distillation column is a tray column or a packed column.

* * * * *